United States Patent [19]
Scheinberg

[11] 3,982,897
[45] Sept. 28, 1976

[54] FILTER AND DETECTOR AND METHODS OF USING SAME IN THE REMOVAL AND DETECTION OF CARBON MONOXIDE FROM, AND IN, A GAS STREAM

[76] Inventor: Israel Herbert Scheinberg, 5447 Palisade Ave., Bronx, N.Y. 10471

[22] Filed: Feb. 19, 1976

[21] Appl. No.: 659,199

Related U.S. Application Data

[63] Continuation-in-part of Ser. No. 292,011, Sept. 25, 1972, which is a continuation-in-part of Ser. No. 151,153, June 8, 1971, abandoned, which is a continuation-in-part of Ser. No. 102,869, Dec. 30, 1970, Pat. No. 3,693,327, which is a continuation-in-part of Ser. No. 85,057, Oct. 29, 1970, abandoned.

[52] U.S. Cl. ............................ 23/232 R; 23/254 R; 55/68; 195/63; 195/68; 195/99; 195/127; 131/173; 131/266
[51] Int. Cl.² ................. A24B 15/02; B01D 39/04; G01N 31/14; G01N 33/16
[58] Field of Search .......... 23/232 R, 254 R; 55/68; 195/63, 68, 99, 127; 131/173, 264, 266

[56] References Cited
UNITED STATES PATENTS

| | | |
|---|---|---|
| 1,826,331 | 10/1931 | Traube ............................ 131/173 X |
| 2,174,349 | 9/1939 | Littlefield ......................... 23/232 R |
| 2,883,990 | 4/1959 | Nichols ........................... 131/264 X |
| 3,286,506 | 11/1966 | Lloyd ............................ 23/254 R X |
| 3,313,305 | 4/1967 | Noznick et al. ................. 131/264 X |
| 3,420,636 | 1/1969 | Robbins ........................... 23/254 R |
| 3,669,126 | 6/1972 | Soussa et al. ................... 131/173 X |
| 3,863,726 | 2/1975 | Chibata et al. .................. 195/63 X |

*Primary Examiner*—Robert M. Reese
*Attorney, Agent, or Firm*—Blum, Moscovitz, Friedman & Kaplan

[57] ABSTRACT

The quantity of carbon monoxide removed from a gas stream by a filter containing hemoglobin is greatly enhanced in quantity when the hemoglobin is accompanied by another factor present in blood. The quantity of carbon monoxide removable from a gas stream by hemoglobin depends upon the equivalent weight of the hemoglobin. However, in the presence of the additional factor, the quantity of carbon monoxide removed is substantially greater than can be accounted for by the stoichiometry of the hemoglobin alone.

41 Claims, 3 Drawing Figures

FILTER AND DETECTOR AND METHODS OF USING SAME IN THE REMOVAL AND DETECTION OF CARBON MONOXIDE FROM, AND IN, A GAS STREAM

CROSS REFERENCE TO RELATED APPLICATIONS

The present application is a Continuation-in-Part of my co-pending application Ser. No. 292,011, filed Sept. 25, 1972, the latter being a Continuation-in-Part application of my now-abandoned Ser. No. 151,153, filed June 8, 1971, and Ser. No. 102,869, filed Dec. 30, 1970, itself a Continuation-in-Part application of then co-pending application Ser. No. 85,057 filed Oct. 29, 1970. Application Ser. No. 102,869 issued to U.S. Pat. No. 3,693,327 of Sept. 26, 1972 and Application Ser. No. 85,057 was abandoned.

BACKGROUND OF THE INVENTION

That carbon monoxide is deadly is widely recognized; however, so far as the general public is concerned the danger presented by this gas is associated primarily with the exhaust products of the internal combustion engine. It is widely known that the consequences of running an automobile engine in a closed garage can be fatal. Also, the public is becoming more and more aware of the fact that carbon monoxide levels resulting from heavy automobile traffic are approaching the danger point in many cities, and in some cities have already passed the danger point for substantial periods of time.

What the public has not as yet come to realize is that carbon monoxide in cigarette smoke appears to be the principal cause of death attributable to cigarette smoking. While the relationship between lung cancer and cigarette smoking, as a result of the publicity given to the results of various studies, has already penetrated mass consciousness, the fact that the carbon monoxide in cigarette smoke presents a far greater danger has not as yet reached the public consciousness. Nevertheless, medical and scientific literature as well as reports of various governmental agencies and the National Academy of Sciences are replete that data causally relating the carbon monoxide content of cigarette smoke to morbidity and death from heart disease. Indeed, the CO absorbed from cigarette smoke by a pregnant woman has been shown to be injurious to her fetus.

It has been well-established that the carbon monoxide level in cigarette smoke can attain a level of 4 percent, or 400 parts per 10,000 parts of air. Studies have shown that where the product of hours of exposure and parts of carbon monoxide per 10,000 parts of air equals 15, a danger to life is present. On this basis, continuous inhalation of cigarette smoke with a 4 percent carbon monoxide content for longer than about 2 minutes endangers the life of a person with a normal heart. However, where the individual suffers from a circulatory deficiency, due, for example, to atherosclerosis, the danger is far greater. In other words, a fatal heart attack may ensue after smoking for a period much shorter than two minutes.

Further to the point of the danger presented by carbon monoxide, individuals exposed to this toxin as the result of being confined in a room in which the air is polluted by a multitude of smokers may also suffer serious consequences. The carbon monoxide content could also rise to dangerous levels for susceptible individuals as well as healthy individuals when travelling through automobile tunnels or when exposed to incomplete combustion products from sources such as ovens, furnaces, chemical operations, etc.

As is evident, it would be highly desirable to be able to absorb the carbon monoxide in tobacco smoke and also to be able to detect the level of carbon monoxide in the ambient atmosphere. Reduction of the carbon monoxide content in cigarette smoke would not only save many lives by way of prevention of heart attack but could also prevent the known reduction in mental acuity believed to be responsible for a substantial proportion of the automobile accidents suffered by cigarette smokers, the reduction in mental acuity being due to inhalation of carbon monoxide in substantial quantities. Further, a simple and effective carbon monoxide detector could warn of the leak of exhaust gases into the passenger compartment of an automobile, such leakage having been responsible for many accidents and deaths.

In my co-pending application having the Ser. No. 292,011, I have described the preparation of ferrous hemoglobin essentially free from methemoglobin. When employing the usual techniques, oxygen coming in contact with ferrous hemoglobin converts it to methemoglobin, so that prior attempts to manufacture hemoglobin free of methemoglobin met with failure. The difficulty was overcome by incorporating a reducing agent with the hemoglobin throughout the process and maintaining the pH of the process solutions between 6.0 and 8.5. Ascorbic acid was found to be particularly satisfactory for the purpose; it was generally found that from 2 to 8 equivalents of ascorbic acid per equivalent of hemoglobin should be used.

Unfortunately, the equivalent weight of hemoglobin is quite high, being in the neighborhood of 16,500. Consequently, the quantity of hemoglobin required to absorb a given quantity of carbon monoxide is relatively high. Some progress has been made in reducing the quantity of absorbent needed by removing part of the protein associated with the heme fraction of the hemoglobin, the rationale behind this step being the fact that it is the iron atom in the heme moiety which loses its ability to complex with oxygen as the result of the presence of carbon monoxide. However, it would be desirable to effect a further reduction in the quantity of carbon monoxide-absorbent required for reacting with a given quantity of carbon monoxide both from the standpoint of the volume occupied by the absorbent, as in a cigarette filter, and from the standpoint of cost.

SUMMARY OF THE INVENTION

Packed red blood cells are obtained most conveniently by centrifugation from the blood of large mammals such as cattle, pigs and horses. However, hemoglobin from other vertebrate and from invertebrate sources as well as from plants (legoglobins) may also be of use.

The packed red blood cells can be used as a CO-absorbent by placing the material in a hookah or hookah-like device. Preferably, an anti-foaming agent such as a silicone is added to prevent foaming during passage of air therethrough. Also, it is desirable that a reducing agent effective for preventing conversion of hemoglobin to methemoglobin by contact with oxygen be present; also, a buffer to hold the pH between the limits of about 6.0 and 8.5 may be added. A phosphate buffer is particularly suitable.

In a second embodiment, the packed cells may be washed free of mother liquor by the use of isotonic saline. In the absence of mother liquor, no anti-foaming agent is needed. However, it is desirable to add buffer and reducing agent to this composition.

In a third embodiment the packed red cells are lysed as by repeated freezing and thawing. The packed red cells are used together with the membranes removed therefrom, these membranes commonly being termed "ghosts." The red cells and the ghosts may be suspended in an aqueous solution containing an anti-foaming agent. Preferably, an effective reducing agent and a buffer to maintain the suspension within the pH range of 6.0 to 8.5 are also present.

The red cells, treated in any of the ways described herein absorb up to about 4 times the quantity of carbon monoxide which can be accounted for on the basis of the hemoglobin present. It appears that a factor other than hemoglobin itself is present and that it is this factor which is responsible for the removal of up to 3 times the quantity of carbon monoxide which the hemoglobin can absorb. This factor, in the presence of oxygen converts carbon monoxide into carbon dioxide.

As the result of the conversion of carbon monoxide to carbon dioxide by said factor, the compositions of the present invention are suitable as a means for detecting carbon monoxide in a gas or gas stream. A gas sample, freed of $CO_2$ if present, is transited through one of the compositions of the present invention and then analyzed for the presence of $CO_2$ as by gas chromatography. The detector can be the usual heated wire or infra-red equipment.

A particularly appropriate way for utilizing the compositions of the present invention is to incorporate them as a filter in a cigarette mouthpiece. An absorbent material such as cellulose or activated carbon can be impregnated with the compositions. Where there is danger of decomposition of the material, as by contact with air, the compositions can be stored in a frangible container in the mouthpiece of a cigarette. For further protection, the cigarettes fashioned as described can be stored under refrigeration.

Accordingly, an object of the present invention is a red blood cell product which can absorb a substantially greater amount of carbon monoxide than can be accounted for by the hemoglobin therein.

Another object of the present invention is a red blood cell composition which can substantially lower the content of carbon monoxide in tobacco smoke.

A further object of the present invention is a red blood cell composition which can be used for detecting the level of carbon monoxide in ambient air.

An important object of the present invention is a method of determining the level of carbon monoxide in ambient air through the use of a composition containing red blood cells.

A significant object of the present invention is a cigarette filter based on the use of a red blood cell composition which is stable for long periods and which is effective for reducing the carbon monoxide content of the smoke from said cigarette.

Yet another object of the present invention is a hookah for use with a red blood cell composition with the purpose of absorbing the carbon monoxide from tobacco smoke passed therethrough.

Still other objects and advantages of the invention will in part be obvious and will in part be apparent from the specification.

The invention accordingly comprises the several steps and the relation of one or more of such steps with respect to each of the others, the relation of constituents, and apparatus embodying the features of construction, combinations and arrangement of parts, all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

As aforenoted, red blood cells contain a factor which increases the absorption of CO substantially above that which can be accounted for on the basis of the hemoglobin content of the cells. Thus, taking the equivalent weight of hemoglobin as 16,500, then one gram of hemoglobin can absorb 22,400/16,500 or about 1.5 cc of CO at normal temperature and pressure. Taking the concentration of CO in air drawn through a cigarette during smoking as 4 percent, one gram of hemoglobin can absorb all of the CO in about 37 cc of air drawn through the cigarette, assuming that the air, once more, is at normal temperature and pressure. However, allowing for the fact that the air is heated in passing through the burning end of the cigarette, it can be assumed that one gram of hemoglobin can completely purify of CO about 45 cc of tobacco smoke. This is equivalent to less than 2 puffs, or substantially less than the number of puffs commonly taken in smoking the usual cigarette. Also, it has been found experimentally that the quantity of CO absorbed by a given weight of hemoglobin prepared in accordance with the procedure described in my co-pending application corresponds closely to the estimate presented.

Figure 1:
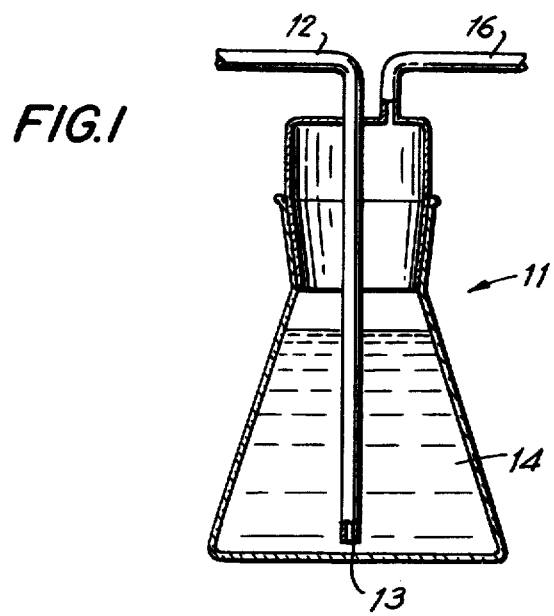
FIG. 1 is a hookah-like device for the absorption of carbon monoxide from a gas stream.

In an experiment representative of the absorptive capacity of the complete red cells as distinguished from the hemoglobin derived therefrom, lysed red blood cells from a dog were placed in an absorber as shown in FIG. 1. Puffs of a gas containing 10 percent of CO together with nitrogen and oxygen in the ratio present in air were introduced into absorption flask 11 through inlet tube 12 and inlet tip 13 into solution 14. The gas exited from absorber 11 through exit tube 16 and was led thence to a conventional gas chromatograph. The synthetic gas contained no $CO_2$ because of the fact that the presence of $CO_2$ renders the determination of residual CO by the gas chromatograph somewhat more difficult and time-consuming.

The pulsing of the CO-containing synthetic mixture was continued until the chromatograph finally showed that the carbon monoxide had come through. Each pulse contained 15 ml of gas at normal temperature and pressure.

When the presence of carbon monoxide was finally detected by the gas chromatograph in the gas exiting from absorber 11, the quantity of carbon monoxide removed by the solution was calculated In this experiment, the absorber contained 15 ml of a 30 percent suspension of hemoglobin from dog blood. The quantity of carbon monoxide removed amounted to almost 4 times that corresponding to the quantity of hemoglobin present. As is evident, another factor which absorbs or otherwise reacts with carbon monoxide must be present.

Red blood cells can be used in a variety of forms for reaction with carbon monoxide. The simplest method is to centrifuge whole blood containing an anticoagulant or blood from which calcium ion has been removed as by ion-exchange, obtaining what is known as packed red blood cells or PRC, consisting of up to about 50 percent red blood cells in mother liquor. This is a viscous suspension. Gas containing CO can be passed directly therethrough for removal of the CO. However, to avoid inconvenient foaming, it is advisable to add a small quantity, usually a few drops, of an anti-foaming agent such as methyl silicone or octyl alcohol.

Usually, oxygen is present in the gas from which CO is to be removed. Consequently, it is desirable that a reducing agent, i.e., a reductant effective for preventing the conversion of hemoglobin to methemoglobin by oxygen be present. Further, it is also desirable that a buffer to hold the pH between 6.0 and 8.5 be present. Ascorbic acid, methylene white and dithionite ion are suitable and effective reductants. A phosphate buffer and tris(hydroxymethyl) aminoethane - HCl buffer are suitable for this purpose. However, it should be noted that any sufficiently strong reducing agent which is effective for preventing the oxidation of hemoglobin to methemoglobin can be used provided that it meets certain obvious requirements. Thus, a reducing agent which requires that the pH of the solution be outside the range of 6.0 to 8.5 cannot be used because of the fact that it will denature the hemoglobin. Furthermore, a reducing agent which can give rise to volatile toxic products when traversed by hot smoke also is inadvisable for use where the smoke is to be inhaled. However, as is evident, such a reducing agent can be used in a test procedure.

For the purposes of the present invention, an effective reductant is one which can maintain hemoglobin in the presence of oxygen essentially free of methemoglobin until said reductant is exhausted, which does not interfere with the activity of hemoglobin or other factors toward CO, and which does not introduce undesirable contaminants into a gas stream passing therethrough as when the stream consists of heated tobacco smoke. Such a reductant may be described as being compatible with the red blood cells and with the purpose served by said cells in the present invention.

Another way in which the red blood cells can be used is by washing the PRC with isotonic saline, and then suspending the PRC in such a solution. It appears that the active factor is contained within the cellular material. As above, it is desirable to include a compatible effective reductant and buffer where it is expected that the solution will come in contact with oxygen. No anti-foaming agent is necessary when the red blood cells are used in this way.

The third way of using the red blood cells is essentially that given in the example above. The packed red blood cells are lysed by any of the standard means such as freezing and thawing, or bringing into contact with distilled water. The membranes or ghosts together with the cellular material are then suspended in an aqueous solution preferably containing an anti-foaming agent. As aforenoted, an effective reductant and a suitable buffer are preferably combined with the cell material.

Figure 2:
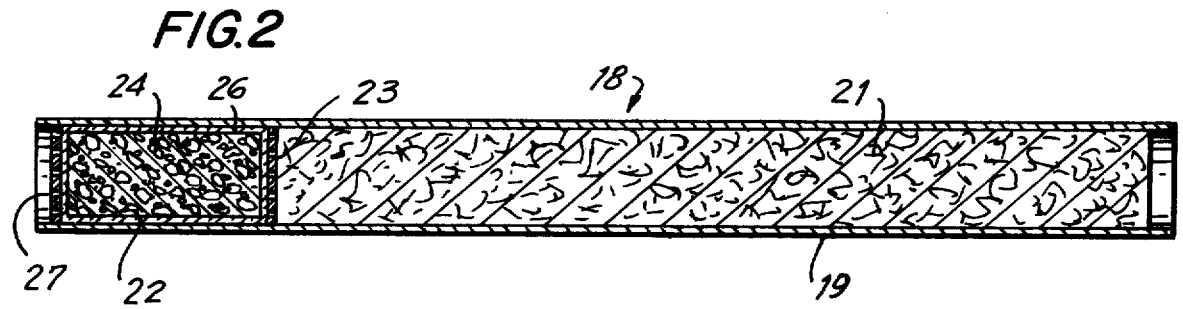
FIG. 2 is a sectional view of a cigarette incorporating an absorbent including red blood cells.

The quantity of reductant used with the cellular material in any of the forms described may vary from about 1 equivalent to 8 equivalents per equivalent of hemoglobin in the absorber.

Where it is desired to remove carbon monoxide from cigarette smoke without using a solution in an absorber as shown in FIG. 1, the cellular material may be made up into a filter to be placed in the mouthpiece of a cigarette. One form of such a filter is shown in FIG. 2 in which a cigarette is represented generally by the reference numeral 18, the cigarette comprising a cigarette paper 19 containing tobacco 21 at the distal end thereof and a filter cartridge 22 in the mouthpiece of the cigarette, the filter 22 and the charge of tobacco 21 being separated by a permeable or perforated barrier 23. The filter charge 22 contains red blood cells in one of the forms described above, the charge being preferably absorbed on an absorbent material such as cellulose floc or activated carbon. The purpose of using such a solid absorbent, of course, is to facilitate transit of tobacco smoke therethrough. The term "tobacco smoke" is used generically to include both the gas stream leaving the burning tobacco and the particulate matter therein.

Since the red blood cells are to be exposed to oxygen in the gas stream, it is preferable that the filter charge also incorporate from 1 to 8 equivalents of an effective reductant per equivalent of hemoglobin in the charge. Further, it is preferable that a buffer capable of maintaining the pH between 6.0 and 8.5 also be present in the charge.

For protection of the red blood cell charge in filter 22 during storage of the cigarettes fitted with such filters, the charge can be encapsulated in a frangible container 26 as shown in FIG. 2. The container should be of a material such that it can be readily broken between the fingers. Alternatively, the container could have a tip (not shown) which can easily be broken off. An additional filter 27 which serves to prevent any glass shards or the like from being inhaled with the gas stream by the smoker may also be incorporated in the cigarette.

As is evident, a similar arrangement can be used for cigars. Alternatively, an absorber such as is shown in FIG. 1 and indicated by the reference numeral 11 may be used in combination with an ordinary cigarette (minus filter 22) or a cigar or a pipe. Another possibility is a pipe (not shown) with a stem so constructed that a filter can be inserted therein as an accompaniment to filling the pipe with a fresh charge of tobacco. Where the red blood cells, whether as part of a cigarette filter or in an absorber solution are to be stored for any substantial period of time, deterioration of the active components may be prevented or, at least, delayed by storing the composition under refrigeration. For example, cigarettes containing such absorber charges could readily be stored under refrigeration. The active life of the charge would be further increased by the encapsulation proposed above.

The terms "absorb," "absorber" and "remove" as used herein with respect to the effect of red blood cells on CO in a gas, are to be understood as encompassing any process which decreases the concentration of CO in said gas, whether the red blood cells function by absorption, or by catalysis of a reaction or by any other means.

The experimental discovery that a charge of red blood cells could remove from a gas stream a quantity of CO up to 4 times as large as could be accounted for on the basis of the hemoglobin present was initially most surprising. However, on further consideration of some seemingly unrelated studies with respect to the physiology of blood, it became apparent that the presence of a factor in blood which could catalyze the conversion of carbon monoxide was not inconsistent with the results of such studies. It has been established that in many animals, including man, there is a small fraction of hemoglobin combined with CO even when the animal is living in a region in which the ambient air is free from any appreciable concentration of CO. The presence of the CO in the blood, then, constitutes proof that there must be endogenous production of CO in the animals. Further, if there were no mechanism for removing the CO at a rate equivalent to that at which it is produced, then the CO would increase to the point where it would be harmful, and, possibly, fatal. The obvious means by which the CO is removed is through an oxidation catalyst in the form of a red blood cell enzyme.

From a teleological or evolutionary standpoint, it is reasonable that such an enzyme should have been developed. This is consistent with the fact that many other red cell enzymes are known, such as glutathione reductase, P-gal-transferase, methemoglobin reductase, etc. Consequently, the existence of an enzyme such as the postulated carbon monoxidase in red blood cells can reasonably be anticipated. The presence of such an enzyme accounts for the observed decreases in the rate and the quantity of CO removal from a gas stream when red blood cells are replaced by purified hemoglobin as the removal agent.

It would appear that the enzyme has not previously been found because it has not been sought, and because studies of hemoglobin and CO reactions have almost always been carried out on purified hemoglobin. As to the present experiments, the CO has been removed from the gas stream in the presence of oxygen, which is consistent with the most likely mechanism, namely, conversion of CO and $CO_2$. Conversion of CO to other products is conceivable. Possible routes are by way of non-oxidative processes such as to cyanate (CNO) for example, or by way of other oxidative processes to products such as formaldehyde, formic acid, or acetic acid. However, it is virtually certain that the actual removal mechanism is by way of oxidation to $CO_2$ since a mechanism for elimination of $CO_2$ from the blood is part of the normal physiologic processes.

Figure 3:
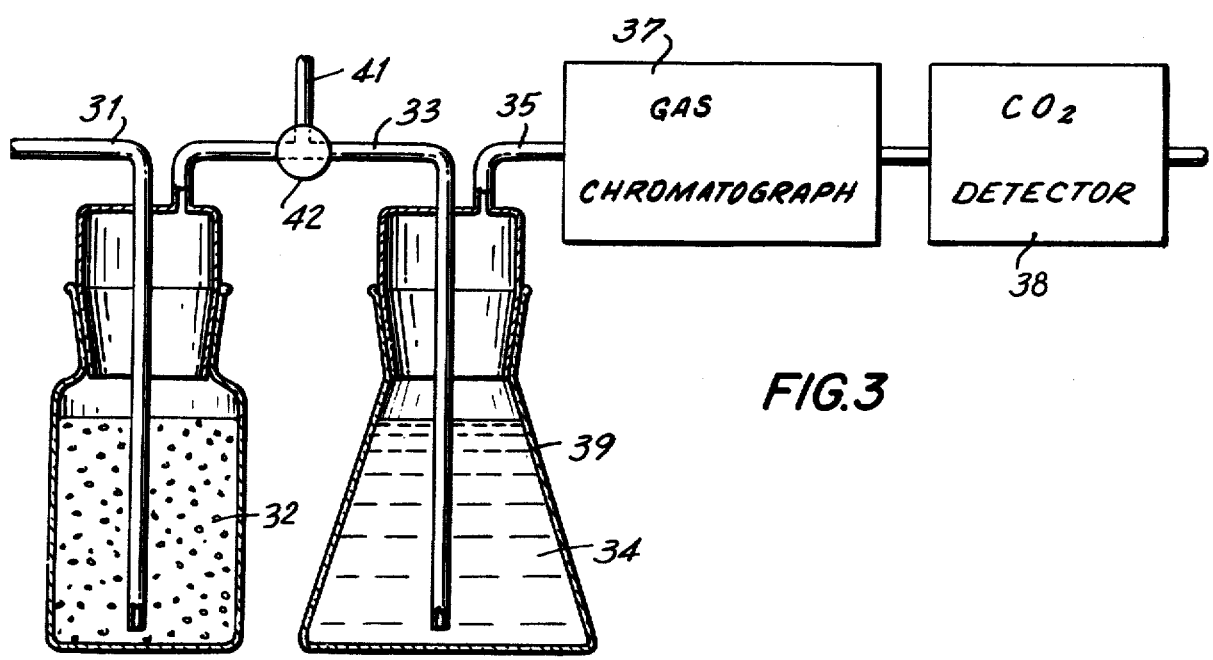
FIG. 3 is an apparatus for determining carbon monoxide in ambient air or a gas stream.

The oxidation of CO to $CO_2$ by the postulated anzyme carbon monoxidase makes it possible to use the red blood cell compositions described above for the detection, quantitatively if desired, of carbon monoxide in a gas. FIG. 3 illustrates apparatus appropriate for this purpose. The gas is introduced by appropriate means (not shown) through inlet tube 31 into $CO_2$-absorber 32 and then through conduit 33 into CO-absorber solution 34. However, the red blood cell composition 34 is now viewed as a reagent for catalyzing the conversion of CO to $CO_2$ by the $O_2$ in the gas stream. The gas stream, now carrying any $CO_2$ produced by oxidation of CO in the gas stream is carried through exit tube 35 into a gas chromatograph represented schematically by box 37 and thence through an appropriate $CO_2$ detector represented schematically by box 38.

Alternatively, the gas stream exiting from absorber-converter 39 can be lead into lime water to produce visible calcium carbonate. Where the gas stream to be analyzed is initially free of $CO_2$ the stream can be introduced into flask 39 through entrance tube 41 and three-way stop-cock 42.

It will thus be seen that the objects set forth above, among those made apparent from the preceding description, are efficiently attained and, since certain changes may be made in the described compositions, in carrying out the above process and in the constructions set forth without departing from the spirit and scope of the invention, it is intended that all matter contained in the above description and shown in the accompanying drawings shall be interpreted as illustrative and not in a limiting sense. Moreover, the invention is not to be limited to the postulated mechanism or by the possible non-existence of the postulated enzyme, since the invention is consistent with applicant's finding that the quantity of CO removed from a gas stream is substantially greater than can be accounted for by the quantity of hemoglobin present.

It is also to be understood that the following claims are intended to cover all of the generic and specific features of the invention herein described, and all statements of the scope of the invention, which, as a matter of language, might be said to fall therebetween.

What is claimed is:

1. A filter for the removal of CO from a gas stream, comprising a container suitable for transit of a gas stream therethrough and a composition including packed red cells in said container.

2. A filter as defined in claim 1, wherein said composition includes an anticoagulant.

3. The filter as defined in claim 1, wherein said composition is free of calcium ion.

4. The filter as defined in claim 1, wherein said filter is a portion of a smoking device.

5. The filter as defined in claim 1, wherein said container includes a frangible member for protecting said composition prior to putting said filter into use.

6. The filter as defined in claim 1, wherein said composition includes an enzyme effective for catalyzing the removal of CO from a gas.

7. The filter as defined in claim 1, further comprising a solid absorbent for holding said composition and facilitating the transit of a gas stream therethrough.

8. The filter as defined in claim 7, wherein said absorbent is selected from the group consisting of absorbent cellulose and activated carbon.

9. A filter as defined in claim 1, wherein said composition includes mother liquor.

10. The filter as defined in claim 9, wherein said composition further includes an effective amount of an anti-foaming agent.

11. The filter as defined in claim 9, wherein said composition includes a buffer for holding the pH of said composition between about 6 and 8.5 and a compatible reductant effective for preventing conversion of hemoglobin to methemoglobin in the presence of oxygen.

12. The filter as defined in claim 11, wherein the ratio of the number of equivalents of said reductant to the number of equivalents of hemoglobin in said red cells is between 1 and 8.

13. The filter as defined in claim 11, wherein said reductant is selected from the group consisting of ascorbic acid, methylene white and dithionite ion.

14. A filter for the removal of CO from a gas stream, comprising a container suitable for transit of a gas stream therethrough, and a composition in said container, said composition including packed red cells free of such components as can be removed by washing said packed red cells with isotonic saline solution.

15. The filter as defined in claim 14, wherein said filter is a portion of a smoking device.

16. The filter as defined in claim 14, wherein said container includes a frangible member for protecting said composition prior to putting said filter into use.

17. The filter as defined in claim 14, wherein said composition includes an enzyme effective for catalyzing the removal of CO from a gas.

18. The filter as defined in claim 14, further comprising a solid absorbent for holding said composition and facilitating the transit of a gas stream therethrough.

19. The filter as defined in claim 18, wherein said absorbent is selected from the group consisting of absorbent cellulose and activated carbon.

20. A filter as defined in claim 14, wherein said composition includes a buffer for holding the pH of said composition between about 6 and 8.5 and a compatible reductant effective for preventing conversion of hemoglobin to methemoglobin in the presence of oxygen.

21. A filter as defined in claim 20, wherein the ratio of the number of equivalents of said reductant to the number of equivalents of hemoglobin in said red cells is between 1 and 8.

22. The filter as defined in claim 20, wherein said reductant is selected from the group consisting of ascorbic acid, methylene white and dithionite ion.

23. A filter for the removal of CO from a gas stream, comprising a container suitable for transit of a gas stream therethrough, and a composition in said container, said composition including red blood cell ghosts and the intracellular material of said red blood cells.

24. The filter as defined in claim 23, wherein said filter is a portion of a smoking device.

25. The filter as defined in claim 23, wherein said composition includes an enzyme effective for catalyzing the removal of CO from a gas.

26. The filter as defined in claim 23, wherein said container includes a frangible member for protecting said composition prior to putting said filter into use.

27. The filter as defined in claim 23, further comprising a solid absorbent for holding said composition and facilitating the transit of a gas stream therethrough.

28. The filter as defined in claim 27, wherein said absorbent is selected from the group consisting of absorbent cellulose and activated carbon.

29. The filter as defined in claim 23, wherein said composition includes a buffer for holding the pH of said composition between about 6 and 8.5 and a compatible reductant effective for preventing conversion of hemoglobin to methemoglobin in the presence of oxygen.

30. The filter as defined in claim 29, wherein the ratio of the number of equivalents of said reductant to the number of equivalents of hemoglobin in said red cells is between 1 and 8.

31. The filter as defined in claim 29, wherein said reductant is selected from the group consisting of ascorbic acid, methylene white and dithionite ion.

32. A method of absorbing CO from a gas stream, comprising the step of passing said gas stream through a container containing a composition including packed red blood cells therein.

33. The method as defined in claim 32, wherein said composition further includes mother liquor.

34. The method as defined in claim 32, wherein said composition further includes a buffer for holding said composition at a pH between 6 and 8.5, and a compatible reductant effective for preventing the conversion of hemoglobin to methemoglobin in the presence of oxygen.

35. A method of removing CO from a gas stream, comprising the step of passing said gas stream through a container containing a composition including packed red cells free of such components as can be removed by washing said packed red cells with isotonic saline.

36. The method as defined in claim 35, wherein said composition further includes a buffer for holding said composition at a pH between 6 and 8.5, and a compatible reductant effective for preventing the conversion of hemoglobin to methemoglobin in the presence of oxygen.

37. A method of absorbing CO from a gas stream, comprising the step of passing said gas stream through a container containing a composition including red blood ghosts and the intracellular material of red blood cells.

38. The method as defined in claim 37, wherein said composition further includes a buffer for holding said composition at a pH between 6 and 8.5, and a compatible reductant effective for preventing the conversion of hemoglobin to methemoglobin in the presence of oxygen.

39. Apparatus for detection of CO in an oxygen-containing gas comprising means for drawing a sample of said gas in sequence through a container containing a blood-derived factor effective for converting CO to $CO_2$ and through means for detecting $CO_2$ in the gas sample leaving said container.

40. The apparatus as defined in claim 39, further comprising a $CO_2$ absorber disposed for removing any $CO_2$ from said gas prior to entry of same into said container.

41. A method of detecting CO in an oxygen-containing gas, comprising the step of drawing a $CO_2$-free sample of said gas through a container containing a blood-derived factor effective for converting CO to $CO_2$ and determining the $CO_2$ produced.

* * * * *